(12) United States Patent
Miller

(10) Patent No.: US 6,281,404 B1
(45) Date of Patent: Aug. 28, 2001

(54) PROCESS FOR OLEFIN ISOMERIZATION

(75) Inventor: Stephen J. Miller, San Francisco, CA (US)

(73) Assignee: Chevron Chemical Company LLC, San Ramon, CA (US)

(*) Notice: Subject to any disclaimer, the term of this patent is extended or adjusted under 35 U.S.C. 154(b) by 0 days.

(21) Appl. No.: 09/507,706

(22) Filed: Feb. 18, 2000

Related U.S. Application Data

(63) Continuation-in-part of application No. 08/746,601, filed on Nov. 13, 1996, now abandoned.

(51) Int. Cl.[7] .................................. C07C 5/23; C07C 5/25
(52) U.S. Cl. ............................ 585/666; 585/667; 585/670
(58) Field of Search ..................................... 585/666, 667, 585/670

(56) References Cited

U.S. PATENT DOCUMENTS

| | | | |
|---|---|---|---|
| 4,749,819 | 6/1988 | Hamilton, Jr. | 585/329 |
| 5,082,986 | 1/1992 | Miller | 585/667 |
| 5,087,793 | 2/1992 | Akiyama et al. | 585/666 |
| 5,114,563 | 5/1992 | Lok et al. | 208/114 |
| 5,191,146 | 3/1993 | Gajda et al. | 585/667 |
| 5,246,566 | 9/1993 | Miller | 208/27 |
| 5,514,362 | 5/1996 | Miller | 423/702 |

*Primary Examiner*—Walter D. Griffin
*Assistant Examiner*—Tam M. Nguyen
(74) *Attorney, Agent, or Firm*—James W. Ambrosius; Reece A. Scott

(57) ABSTRACT

A process for the double bond isomerization of olefinic feed compounds is provided comprising contacting the olefinic feed compounds and a catalyst under reaction conditions sufficient to produce double bond isomerization, wherein the catalyst is an aluminophosphate-containing molecular sieve with pores having a diameter in the range of about 3.8 Å to about 5 Å. The process provides high conversion of normal alpha-olefins and high selectivity for linear internal olefins.

15 Claims, 1 Drawing Sheet

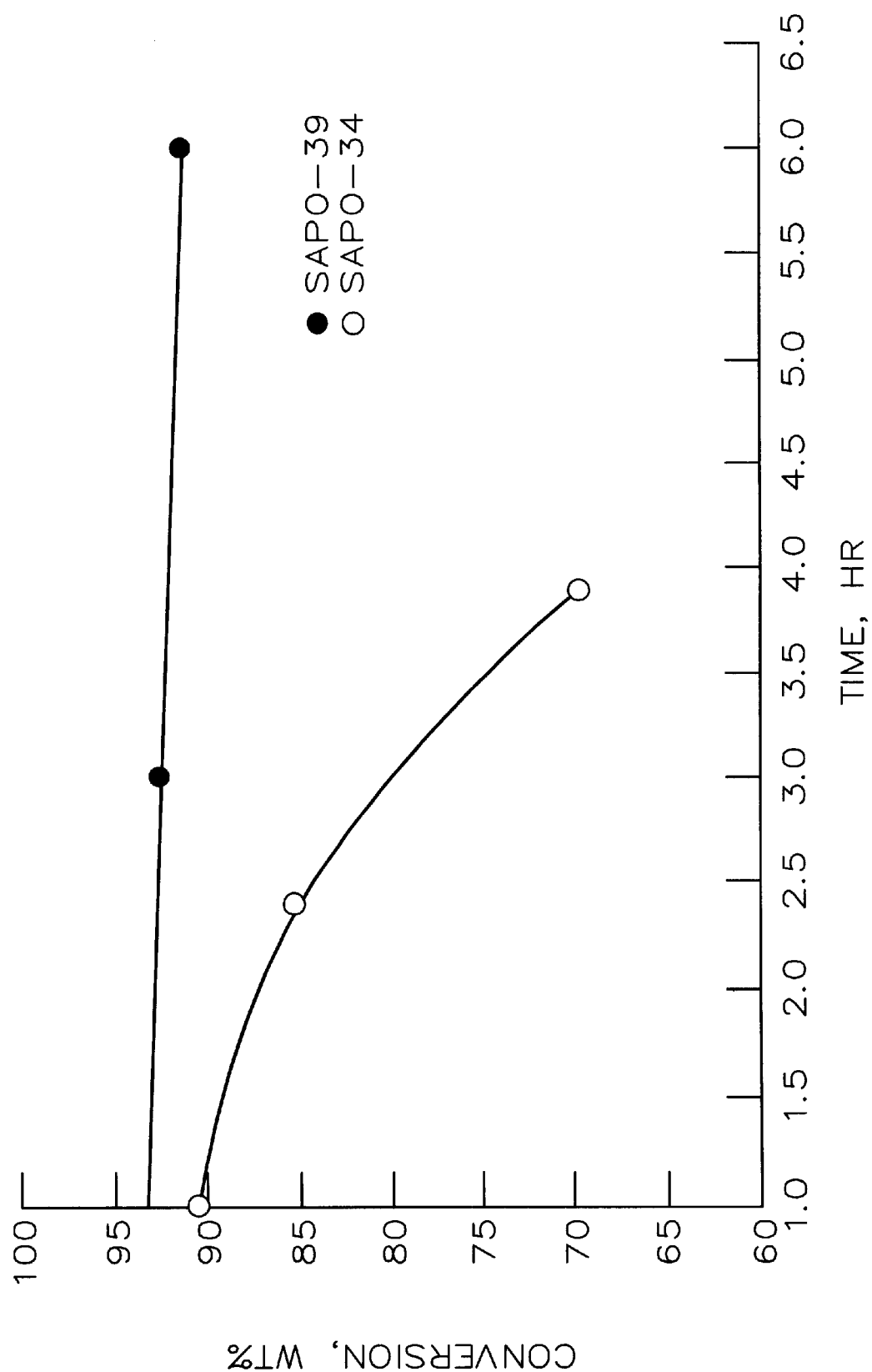

PROCESS FOR OLEFIN ISOMERIZATION

CROSS REFERENCE TO RELATED APPLICATION

This Application is a continuation-in-part of U.S. patent application Ser. No. 08/746,601 filed Nov. 13, 1996, now abandoned.

FIELD OF THE INVENTION

This invention relates to a process for the double bond isomerization of olefinic feed compounds in the presence of a molecular sieve of specific pore geometry.

BACKGROUND OF THE INVENTION

Molecular sieves are crystalline materials which have distinct crystal frameworks with ordered pore structures and cavities. Aluminosilicate zeolite-type molecular sieves useful as adsorbents or catalysts are known in the art and now comprise over 150 species of both naturally occurring and synthetic compositions. In general, the zeolites have frameworks formed from $AlO_4$-and $SiO_4$ tetrahedra joined by the sharing of oxygen atoms. Such zeolites have a significant ion-exchange capacity and are capable of reversibly desorbing an adsorbed phase which is dispersed through the internal voids of the crystal without displacing any atoms which make up the permanent crystal structure.

Non-zeolite molecular sieves comprising aluminophosphates are also known to be useful as adsorbents or catalysts. These non-zeolite molecular sieves generally contain $[AlO_2]$ and $[PO_2]$ tetrahedral units as essential framework constituents, and at least one additional element as a framework tetrahedral unit.

Various catalysts are known for their use in the double bond isomerization of olefinic feed compounds. However, many of these catalysts produce substantial amounts of polymer and/or skeletal isomerized product, i.e., branched olefins. For some applications, such as preparing internal olefins for alkylation reactions, it is desirable to limit branched products to the least amount possible. Therefore, for certain applications, it is desirable to use a catalyst which is selective for the isomerization of the double bond without the isomerization of the skeletal structure.

SUMMARY OF THE INVENTION

It is an object of the present invention to provide a process for the double bond isomerization of olefinic compounds.

It is another object of the present invention to provide a process with high conversion rates.

It is another object of the present invention to provide a process with high selectivity for internal linear olefins.

It is another object of the present invention to provide a process which produces low amounts of branched olefins.

It is another object of the present invention to provide a process with reduced catalyst coking.

It is another object of the present invention to provide a process with increased catalyst life span.

A process for the double bond isomerization of normal alpha olefins having from 4 to 50 carbon atoms, the process which comprises contacting the alpha olefins with a catalyst under reaction conditions sufficient to produce double bond isomerization, wherein the catalyst comprises an aluminophosphate-containing molecular sieve with one-dimensional pores having a diameter in the range of from about 3.8 Å to about 5.0 Å and wherein said catalyst at a conversion rate of 60% will give a yield of branched olefins of less than 3.5 weight % with a feed of 1-pentene. Preferably the catalyst will contain an element which form oxide linkages in tetrahedral coordination with the aluminum and phosphorous in the crystalline network. The element forming the oxide linkage generally will be selected from the group consisting of silicon, arsenic, beryllium, boron, chromium, cobalt, gallium, germanium, iron, lithium, magnesium, manganese, titanium, vanadium, and zinc. Particularly preferred is silicon. In practicing the present invention the catalyst will preferably be silica-containing aluminophosphate molecular sieve which is usually referred to as a SAPO. Examples of catalyst useful in carrying out the process of the present invention are SAPO-22 and SAPO-39, with SAPO-39 being particularly preferred.

BRIEF DESCRIPTION OF THE DRAWING

The FIGURE is a graphic representation of the percent conversion versus time for a catalyst having one-dimensional pores, SAPO-39, compared to a catalyst having three-dimensional pores, SAPO-34.

DETAILED DESCRIPTION OF THE INVENTION

The present invention provides a process for the double bond isomerization of olefinic feed compounds employing particular aluminophosphate-containing molecular sieves.

The catalysts of the present invention are aluminophosphate-containing molecular sieves which have a pore size in the range of from about 3.8 Å to about 5.0 Å, preferably in the range of from 3.8 Å to 4.7 Å.

The effective pore size of the molecular sieves can be measured using standard adsorption techniques and hydrocarbonaceous compounds of known minimum kinetic diameters. See Breck, *Zeolite Molecular Sieves*, 1974 (Chapter 8); Anderson et al., *J. Catalysis* 58, 114 (1979); and U.S. Pat. No. 4,440,871, the pertinent disclosures of which are incorporated herein by reference.

The pores of the present catalyst are one-dimensional, meaning they are parallel and are not interconnected. One-dimensional pores exhibit less coking problems during the reaction, and therefore an extended catalyst life span. Three-dimensional sieves have intersecting pores which can lead to increased coke, causing deactivation of the catalyst.

The aluminophosphate-containing molecular sieves are commonly known as "non-zeolite molecular sieves". Aluminophosphate-containing molecular sieves contain $[AlO_2]$ and $[PO_2]$ tetrahedral units joined by the sharing of the corner oxygen atoms and characterized by having pore openings of uniform dimensions.

The aluminophosphate-containing molecular sieve can optionally contain silicon and/or one or more other elements which will form oxide linkages in tetrahedral coordination with aluminum and phosphorous in a crystalline framework. Suitable elements other than silicon include arsenic, beryllium, boron, chromium, cobalt, gallium, germanium, iron, lithium, magnesium, manganese, titanium, vanadium and zinc.

Examples of suitable aluminophosphate-containing molecular sieves having one-dimensional pores in the preferred range include silicon-containing SAPO-22 and SAPO-39. An example of a magnesium-containing catalyst useful in carrying out the present invention is MAPO-39. SAPO-39 is especially preferred due to excellent results in conversion and selectivity.

Suitable catalysts can be prepared by methods known in the art such as disclosed in U.S. Pat. Nos. 4,440,871; 4,567,029; 4,663,139 and 5,514,362, the disclosures of which are hereby incorporated by reference in their entirety. The preparation of aluminophosphate-containing compositions is disclosed in U.S. Pat. No. 4,663,139. The preparation of silicon-containing aluminophosphate compositions SAPO-39 is disclosed in U.S. Pat. No. 5,514,362. The preparation of the magnesium-containing aluminophosphate composition MAPO-39, as well as aluminophosphate compositions containing manganese, cobalt or zinc, is disclosed in U.S. Pat. No. 4,567,029. The preparation of non-zeolitic molecular sieve compositions is disclosed in U.S. Pat. No. 4,973,785. The elements disclosed include arsenic, beryllium, boron, chromium, cobalt, gallium, germanium, iron, lithium, magnesium, manganese, titanium, vanadium and zinc.

Aluminophosphate-containing molecular sieves are typically prepared by hydrothermal crystallization of a reaction mixture containing water, a reactive source of aluminum, such as pseudo-boehmite, Al(OH)3, or an aluminum alkoxide, a reactive source of phosphorus, such as phosphoric acid, and an organic templating agent, such as an alkyl amine.

The reaction mixture is placed in a reaction vessel and heated until crystallized, usually at a temperature of at least about 80° C., preferably between 100° C. and 200° C., and a period of from about 2 hours to 2 weeks. The solid crystalline reaction product is then recovered by any convenient method, such as filtration or centrifugation, washed with water and dried in air at a temperature between ambient and about 150° C.

The catalyst can be calcined at a temperature sufficiently high to dehydrate and/or remove at least a portion of the organic templating agent present in the intracrystalline pore system. Generally, the calcining temperature will be in the range of from 200° C. to 800° C.

In order to maintain efficient double bond isomerization, it is preferred that hydrogenation promoters are not present in the catalyst. Therefore, it is preferred that the catalyst is essentially free of hydrogenation promoters.

The catalyst can contain metals which reduce the number of strong acid sites on the catalyst and thereby lower the selectivity for cracking versus double bond isomerization. Especially preferred are the Group IIA metals such as magnesium and calcium.

Strong acidity can also be reduced by introducing nitrogen compounds, e.g., $NH_3$ or organic nitrogen compounds, into the feed; however, the total nitrogen content should be less than 50 ppm, preferably less than 10 ppm.

It is preferred that relatively small crystal size catalyst be utilized in practicing the invention. Suitably, the average crystal size is no greater than about $10\mu$, preferably no more than about $1\mu$ and still more preferably no more than about $0.5\mu$.

The physical form of the catalyst depends on the type of catalytic reactor being employed and can be in the form of a granule or powder, and is preferably compacted into a more readily usable form (e.g., larger agglomerates), usually with a silica or alumina binder for fluidized bed reaction, or pills, prills, spheres, extrudates, or other shapes of controlled size to accord adequate catalyst-reactant contact. The catalyst can be employed either as a fluidized catalyst, or in a fixed or moving bed, and in one or more reaction stages.

The aluminophosphate-containing molecular sieve may be used as a catalyst, without additional forming when the particles recovered from the crystallization step are of a size and shape desired for the ultimate catalyst. The molecular sieve can be composited with other materials resistant to temperatures and other conditions employed in the isomerization process. Such matrix materials include active and inactive materials and synthetic or naturally occurring zeolites as well as inorganic materials such as clays, silica and metal oxides. The latter may be either naturally occurring or in the form of gelatinous precipitates, sols or gels including mixtures of silica and metal oxides.

Inactive materials suitably serve as diluents to control the amount of conversion in the isomerization process so that products can be obtained economically without employing other means for controlling the rate of reaction. The molecular sieve may be incorporated into naturally occurring clays, e.g., bentonite and kaolin. These materials, i.e., clays, oxides, etc., function in part, as binders for the catalyst. It is desirable to provide a catalyst having good crush strength because the catalyst is often subjected to rough handling. This tends to break the catalyst down into powder-like materials which cause problems in processing.

Naturally occurring clays which can be composited with the catalyst include the montmorillonite and kaolin families, which families include the sub-bentonites, and the kaolins commonly known as Dixie, McNamee, Georgia and Florida clays or others in which the main mineral constituent is halloysite, kaolinite, dickite, nacrite or anauxite. Fibrous clays such as halloysite, sepiolite and attapulgite can also be used as supports. Such clays can be used in the raw state as originally mined or initially subjected to calcination, acid treatment or chemical modification.

In addition to the foregoing materials, the molecular sieve can be composited with porous matrix materials and mixtures of matrix materials such as silica, alumina, titania, magnesia, silica-alumina, silica-magnesia, silica-zirconia, silica-thoria, silica-beryllia, silica-titania, titania-zirconia as well as ternary compositions such as silica-alumina-thoria, silica-alumina-titania, silica-alumina-magnesia and silica-magnesia-zirconia. The matrix can be in the form of a cogel.

The catalyst can also be composited with zeolites such as synthetic and natural faujasites (e.g., X and Y), erionites, and mordenites. The catalyst can also be composited with purely synthetic zeolites such as those of the ZSM series. The combination of zeolites can also be composited in a porous inorganic matrix.

The double bond isomerization can be conducted by contacting the feed with a fixed stationary bed of catalyst, with a fixed fluidized bed, or with a transport bed. A simple and therefore preferred configuration is a trickle-bed operation in which the feed is allowed to trickle through a stationary fixed bed.

Typically, the olefinic feed compounds are alpha-olefins, preferably normal alpha-olefins. Generally, the olefinic feed compounds contain from 4 to 50 carbon atoms, preferably from 4 to 40 carbon atoms. The feed streams can be obtained from any suitable source. The olefins can be prepared by ethylene polymerization or Fischer-Tropsch synthesis, by wax cracking or from feeds containing normal alpha-olefins produced in petroleum refining.

While the process of the invention can be practiced with utility when the feed contains organic nitrogen-containing impurities, it is preferred that the organic nitrogen content of the feed be less than about 50 ppmw (parts per million by weight), more preferably less than about 10 ppmw. Particularly good results, in terms of activity and length of catalyst cycle (period between successive regenerations or startup and first regeneration) are experienced when the feed contains less than about 10 ppmw of organic nitrogen.

Reaction conditions for the process can vary broadly depending on the particular compounds being isomerized and the catalyst employed. Reaction conditions include the time, temperature and pressure sufficient to produce double bond isomerization of the olefinic feed compounds.

Preferred operating conditions are those which result in substantially no olefin cracking. By substantially no olefin cracking is meant very low yield loss, less than 10 weight percent, preferably less than 5 weight percent and more preferably less than 2 weight percent of the feed is cracked to products having fewer carbon atoms than the feed. In a preferred embodiment, greater than 90 weight percent, preferably greater than 95 weight percent and more preferably greater than 98 weight percent of the product is within the boiling range of the olefin feed.

Generally, reaction temperatures are in the range of from about 50° C. to about 500° C., preferably from about 100° C. to about 400° C., and more preferably from 150° C. to 350° C.

The liquid hourly space velocity (LHSV) can vary broadly but will generally be in the range of from about 0.1 to about 20, preferably in the range of from about 0.1 to about 10, and more preferably in the range of from 0.1 to 5.

Reaction pressures are not critical and will depend on the temperature, reactants, and equipment employed. Typically, the pressure is in the range of from about atmospheric to about 2000 psig, preferably from atmospheric to 500 psig.

The reaction may be carried out in the presence or absence of added hydrogen, where the added hydrogen may be used to enhance catalyst stability by suppressing coke formation. When hydrogen is added, the reactor conditions are adjusted to minimize the loss of olefins through hydrogenation. The reactor feed may also be mixed with an inert diluent such as $N_2$ during the reaction.

When the feed is 1-pentene, under the general reaction conditions described above, and at a conversion rate of 60%, catalysts within the scope of the invention will produce a product containing less than about 3.5 weight % of branched olefins. At higher conversion rates, the amount of branched olefins present in the isomerized product may increase somewhat above this FIGURE, but the amount of branched material still would be expected to be significantly less than would be otherwise be present when using a catalyst outside of the scope of the invention. Also for feeds containing higher molecular weight normal olefins, the amount of branched material will increase in the product, however, the amount of branched material would be expected to be significantly less than the amount present when other catalysts are used in carrying out the invention. For this reason, it is important that it is understood that isomerization of 1-pentene at a 60% conversion rate is a useful index when comparing the performance of different catalysts.

The isomerized olefins are useful in producing sizings, inks, alkylate products, drilling fluids and for other known uses.

The following examples serve to show the present invention in detail by way of illustration and not by way of limitation.

EXAMPLES

Example 1

SAPO-39, a small pore aluminophosphate-containing molecular sieve catalyst, was prepared by mixing 92 g 86% $H_3PO_4$ with 19 g Catapal alumina (pseudo boehmite, 73 wt % $Al_2O_3$, 27 wt % $H_2O$) for 10 minutes. To the mixture was added 8 g silica (Cab-O-Sil M-5, 91 wt % $SiO_2$, 9 wt % $H_2O$) and 80 grams peptized and neutralized Catapal alumina (35 wt % $Al_2O_3$, 65 wt % $H_2O$). The mixture was stirred for about 1.3 hours. Then 36 g di-n-propylamine were added, followed by 37 grams of Catapal alumina. The mix was then extruded through a 1/16 inch die. Volatiles content of the extrudate was 49.0 wt %. The extrudate was placed in a Teflon bottle in a stainless steel pressure vessel and heated at 190° C. and autogenous pressure for two days. The extrudate was washed with water, dried in a vacuum oven overnight at 120° C., and then calcined in air for six hours at 600° C. X-ray diffraction analysis showed the extrudate to consist primarily of SAPO-39.

The catalyst was used to isomerize 1-pentene at 400° F., 1 LHSV, and 12 psig, along with a nitrogen diluent at a molar ratio of nitrogen to pentene of 2.6. The results are shown in Table I

Example 2

SAPO-34, a small pore aluminophosphate-containing molecular sieve catalyst, was prepared according to U.S. Patent No.4,440,871. The SAPO-34 catalyst was used to isomerize 1-pentene at the same conditions as in Example 1, except the temperature was raised to 450° F. to achieve about the same conversion as with the catalyst of Example 1. The results are shown in Table I.

TABLE I

Isomerization of 1-Pentene

| | Catalyst | | | |
|---|---|---|---|---|
| | SAPO-39 | SAPO-39 | SAPO-34 | SAPO-34 |
| Temperature 0° F. | 400 | 400 | 450 | 450 |
| Conversion Wt % | 65.4 | 52.9 | 66.1 | 48.7 |
| Selectivity Wt % | | | | |
| t-2-pentene | 67.3 | 66.7 | 58.2 | 55.9 |
| c-2-pentene | 28.1 | 26.3 | 38.3 | 34.7 |
| Total 2-pentene | 95.4 | 93.0 | 96.5 | 90.6 |
| 3-me-1-butene | <0.1 | <0.1 | 0.1 | 0.2 |
| 2-me-1-butene | 0.3 | 0.5 | 0.8 | 0.8 |
| 2-me-2-butene | 1.3 | 1.6 | 3.2 | 3.6 |
| Total branched butene | 1.6 | 2.1 | 4.1 | 4.6 |

This Table illustrates that SAPO-39 at a conversion rate in the general range of 60% when 1-pentene is the feed will produce less than half the amount of branched material as SAPO-34.

Example 3

The intermediate pore aluminophosphate-containing molecular sieve catalyst $ALPO_4$-11 was prepared according to U.S. Pat. No. 4,310,440. SAPO-39 was prepared as disclosed in Example 1. The catalysts were used to isomerize 1-pentene at the same conditions as in Example 1 except that the temperature for ALPO-11 was raised to 500° F. to achieve the same 1-pentene conversion.

TABLE II

Isomerization of 1-Pentene

| Catalyst | SAPO-39 | ALPO-11 |
|---|---|---|
| Temperature, ° F. | 400 | 500 |
| 1-pentene | 9.3 | 9.1 |
| trans-2-pentene | 61.1 | 52.5 |
| cis-2-pentene | 25.5 | 22.9 |
| Total 2-pentene | 86.6 | 75.4 |
| 3-methyl-1-butene | 0.1 | 0.3 |
| 2-methyl-1-butene | 0.5 | 2.7 |
| 2-methyl-2-butene | 1.2 | 10.2 |
| Total branched pentene | 1.8 | 13.2 |
| Isomerized pentane | 0.9 | 0.8 |
| Normal pentane | 1.3 | 1.5 |

The results in Table II show significantly higher branched products in the process employing ALPO-11.

Example 4

The catalysts SAPO-39 and SAPO-11 were prepared as described in Example 1 and 3, respectively. The catalysts were used to isomerize $C_{20}$–$C_{24}$ at 0 psig and 3 LHSV. The results are shown in Table III.

TABLE III

Isomerization of $C_{20}$–$C_{24}$ Normal Alpha-Olefins

| | Catalyst | | | | |
|---|---|---|---|---|---|
| | SAPO-39 | SAPO-39 | SAPO-39 | SAPO-11 | SAPO-11 |
| Temperature 0° C. | 210 | 240 | 250 | 180 | 190 |
| Percent Conversion | 75.8 | 97.3 | 99.6 | 69.4 | 83.2 |
| Percent Branched Olefin | 5.8 | 10.8 | 18.4 | 11.6 | 19.9 |

This Table illustrates that as the amount of conversion increases, the amount of branched material in the final product also increases. However, at comparable conversion rates, SAPO-39 used in the practice of the present invention continues to show less skeletal isomerization than illustrated by SAPO-11.

Example 5

The catalyst of Example 1, SAPO-39, a catalyst having one-dimensional pores, and the catalyst of Example 2, SAPO-34, a catalyst having three-dimensional pores, were compared for isomerizing 1-pentene at 1.1 WHSV, 204° C., 12 psig and 2.7 $N_2$/HC. The FIGURE shows a much lower fouling rate for the SAPO-39 catalyst containing one-dimensional pores compared to the SAPO-34 catalyst containing three-dimensional pores.

What is claimed is:

1. A process for the double bond isomerization of normal alpha olefins having from 4 to 50 carbon atoms, the process which comprises contacting the normal alpha olefins with a catalyst under reaction conditions sufficient to produce double bond isomerization, wherein the catalyst comprises an aluminophosphate-containing molecular sieve with one-dimensional pores having a diameter in the range of from about 3.8 Å to about 5.0 Å and wherein said catalyst at a conversion rate of 60% will give a yield of branched olefins of less than 3.5 weight % with a feed of 1-pentene.

2. The process according to claim 1 wherein the pores have a diameter in the range of from 3.8 Å to 4.7 Å.

3. The process according to claim 1 wherein the catalyst further comprises an element which will form oxide linkages in tetrahedral coordination with aluminum and phosphorous in a crystalline framework.

4. The process according to claim 3 wherein the element is selected from the group consisting of silicon, arsenic, beryllium, boron, chromium, cobalt, gallium, germanium, iron, lithium, magnesium, manganese, titanium, vanadium or zinc.

5. The process according to claim 4 wherein the element is silicon or magnesium.

6. The process according to claim 1 wherein the catalyst is SAPO-22, SAPO-39, or MAPO-39.

7. The process according to claim 6 wherein the catalyst is SAPO-22 or SAPO-39.

8. The process according to claim 7 wherein the catalyst is SAPO-39.

9. The process according to claim 1 wherein the catalyst is essentially free of hydrogenation promoters.

10. The process according to claim 1 wherein the normal alpha olefins contain from 4 to 40 carbon atoms.

11. The process according to claim 1 wherein the reaction conditions include a temperature in the range of from about 50° C. to about 500° C.

12. The process according to claim 11 wherein the reaction conditions include a temperature in the range of from about 100° C. to about 400° C.

13. The process according to claim 12 wherein the reaction conditions include a temperature of 150° C. to 350° C.

14. The process according to claim 11 wherein the reaction conditions include a liquid hourly space velocity in the range of from about 0.1 to about 20.

15. The process according to claim 14 wherein the reaction conditions include a liquid hourly space velocity in the range of from about 0.1 to about 10.

* * * * *